US00RE35192E

United States Patent [19]

Reese

[11] E Patent Number: Re. 35,192

[45] Reissued Date of Patent: Mar. 26, 1996

[54] POST-SURGICAL ANESTHESIA AT A CONTINUOUS AND PROGRESSIVELY DECREASING ADMINISTRATION RATE

[75] Inventor: H. William Reese, Tempe, Ariz.

[73] Assignee: Phoenix Surgical Products, Inc., Peoria, Ariz.

[21] Appl. No.: 319,148

[22] Filed: Oct. 6, 1994

Related U.S. Patent Documents

Reissue of:

[64] Patent No.: 5,078,679
Issued: Jan. 7, 1992
Appl. No.: 611,976
Filed: Nov. 13, 1990

U.S. Applications:

[63] Continuation of Ser. No. 78,632, Jun. 21, 1993, abandoned.

[51] Int. Cl.[6] ..... A61M 31/00

[52] U.S. Cl. ..... 604/51; 604/135; 604/121; 604/93

[58] Field of Search ..... 604/49, 50, 51, 604/131, 134, 135

[56] References Cited

U.S. PATENT DOCUMENTS

| | | | |
|---|---|---|---|
| 3,598,119 | 8/1971 | White | 604/51 |
| 3,854,477 | 12/1974 | Smith | 604/51 |
| 4,381,006 | 4/1983 | Genese | 128/218 A |
| 4,597,754 | 7/1986 | Thill et al. | 604/154 |
| 4,813,926 | 3/1989 | Kerwin | 604/51 |
| 4,813,937 | 3/1989 | Vaillancourt | 604/131 |
| 4,863,429 | 9/1989 | Baldwin | 604/135 |
| 4,874,386 | 10/1989 | O'Boyle | 604/246 |
| 4,966,585 | 10/1990 | Gangemi | 604/131 |
| 4,997,420 | 3/1991 | LeFevre | 604/121 |
| 5,069,668 | 12/1991 | Boydman | 604/121 |
| 5,084,021 | 1/1992 | Baldwin | 604/131 |
| 5,106,376 | 4/1992 | Mononen et al. | 604/51 |

*Primary Examiner*—John G. Weiss
*Attorney, Agent, or Firm*—Antonio R. Durando; Harry M. Weiss

[57] ABSTRACT

A method of administering post-operative anesthesia directly to the surgical site through a catheter introduced into the site during the post-operative procedure. The flow of medication into the catheter is regulated by a micro-bore cannula that insures delivery at very small rates. The plunger of a spring-loaded syringe creates the pressure that causes the medication to flow through the cannula and catheter into the wound. Because of the spring's nonlinear characteristics within the range of stroke of the plunger, the pressure exerted on the liquid gradually decreases with the expansion of the spring. By appropriately sizing the spring and the inside diameter of the cannula, a device is developed that administers the required dosages of anesthetic continuously and at decreasing rates.

16 Claims, 1 Drawing Sheet

POST-SURGICAL ANESTHESIA AT A CONTINUOUS AND PROGRESSIVELY DECREASING ADMINISTRATION RATE

Matter enclosed in heavy brackets [ ] appears in the original patent but forms no part of this reissue specification; matter printed in italics indicates the additions made by reissue.

*This application is a continuation of 08/078,632, filed Jun. 21, 1993, and is now abandoned, which is a reissue of 07/611,976, filed Nov. 13, 1990, and is U.S. Pat. No. 5,078,679.*

BACKGROUND OF THE INVENTION

1. Field of the Invention

This invention is related in general to the field of drug infusions and, in particular, to the area of administration of post-operative anesthesia. The invention provides a novel technique and equipment to inject liquid anesthetics directly into the surgical site on a continuous basis.

2. Description of the Prior Art

Post-operative pain normally requires the injection of anesthetic medication into the area affected by the surgical procedure in order to alleviate the patient's discomfort and facilitate a successful recovery. Typically, care providers inject a liquid anesthetic directly into the surgical site for a number of days after the operation. This procedure necessitates a new needle puncture in an already sensitive area with each administration, with the obvious result of pain exacerbation and an increased potential for infection. Alternatively, post-operative pain can be alleviated with the administration of narcotics, but this approach is generally not favored because of their side effects.

When an anesthetic is administered locally, normally the dosage at each injection is reduced over a period of a few days after the operation because of the decreasing level of discomfort and the corresponding smaller need for anesthesia. This requires that accurate records be kept to avoid confusion concerning the type of medication and dosages used at each time. Therefore, in addition to the pain and trauma inflicted to the patient by the repeated needle punctures, the potential for error is increased because of the recurring human involvement. Thus, there is a need for an infusion apparatus designed to administer the total dosage of anesthetic required for post-operative treatment on a continuous and progressively decreasing basis through a single injection site in the surgical wound.

BRIEF SUMMARY OF THE INVENTION

One objective of this invention is the development of a device for the administration of post-operative anesthesia locally and through a single injection site. This is obtained by providing a catheter that is introduced into the surgical wound and is used as the sole channel for infusing the required amount of pain relieving medication.

Another objective of the invention is an apparatus that dispenses the medication on a continuous basis. Thus, this device involves a spring-loaded syringe capable of holding the entire dosage of anesthetic required to be infused during the course of treatment and of delivering it continuously as a result of constant pressure applied by a spring on the syringe plunger.

A further goal of the invention is the gradual decrease of the rate of delivery of anesthetic according to a predetermined administration schedule. Therefore, the rate of flow out of the syringe is controlled by a specially designed length of micro-bore tubing and a variable pressure spring that result in the desired rate of delivery.

Yet another goal of the invention is a unit that can be set up as part of the post-operative procedure and left in place during the entire period of administration. To that end, the apparatus includes a catheter placement needle to provide access to the surgical site through a single procedure, and an injection port for charging the spring-loaded syringe with the total dosage of required medication.

A final objective is the easy and economical manufacture of the device according to the above stated criteria. This is achieved by using commercially available components and materials, modified only to the extent necessary to fit the requirements of the invention.

Therefore, according to these and other objectives, the present invention describes an apparatus for administering post-operative anesthesia directly to the surgical site through a catheter introduced into the site during the post-operative procedure. The flow of medication into the catheter is regulated by a micro-bore cannula that insures delivery at very small rates. The plunger of a spring-loaded syringe creates the pressure that causes the medication to flow through the cannula and catheter into the wound. Because of the spring's nonlinear characteristics within the range of stroke of the plunger, the pressure exerted on the liquid gradually decreases with the expansion of the spring. By appropriately sizing the spring and the inside diameter of the cannula, a device is developed that administers the required dosages of anesthetic continuously and at decreasing rates.

Various other purposes and advantages of the invention will become clear from its description in the specifications that follow and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

This invention consists of the application of simple mechanical principles in combination with known structural components to achieve a practical and economical design for an infusion device with the properties described above. The main point of the invention lies in the recognition of the advantages involved with the continuous administration of post-operative anesthesia and the fact that it can be achieved in an optimal manner by gradually reducing the delivery rate according to a desired, predetermined schedule.

Figure 1:
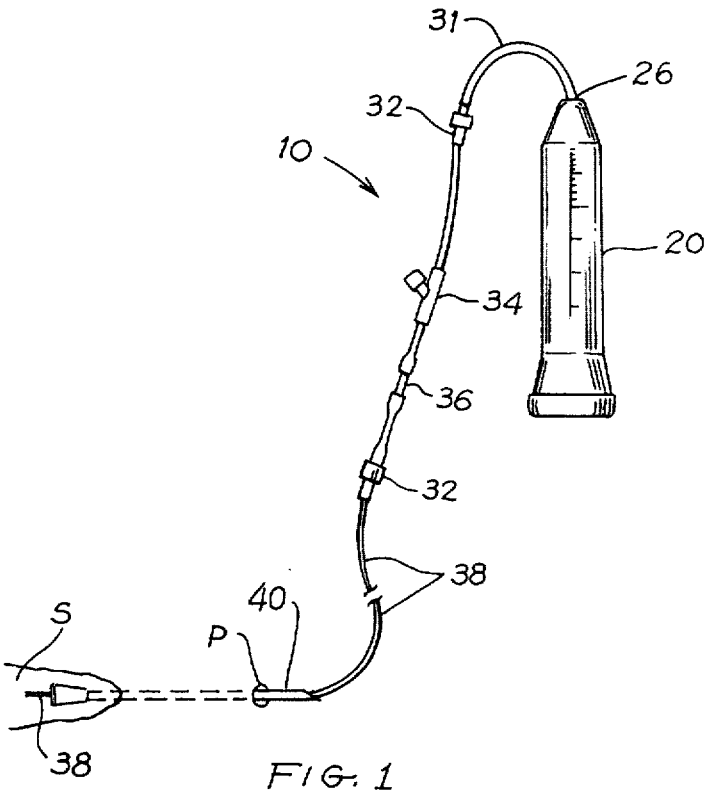
FIG. 1 is a schematic representation of the apparatus of this invention as used to administer medication to a patient.

Referring to the drawings, wherein like parts are designated throughout with like numerals and symbols, FIG. 1 illustrates the apparatus 10 of this invention with its several components assembled for use. A spring-loaded syringe 20, integrally connected through its tip 26 to standard medical tubing 31, is used both as reservoir and pump. In the preferred embodiment of the invention, a 50 cc syringe is employed because that capacity corresponds with the normal requirements of total anesthetic administration during the post-operative period. As illustrated in more detail in FIG. 2, the plunger 22 of the syringe is connected in working relationship with a spring 30 that exerts pressure in the direction of discharge. As the syringe is filled with medication by injection through an apposite injection port 34, the stopper 23 of the plunger 22 is pushed in an outward direction in the barrel 24, and the spring 30 is compressed and loaded into a charged position for exerting pressure on the liquid. When the outlet pressure of the syringe is released, the spring pressure causes the medication to flow out of the syringe continuously until the syringe becomes empty at the end of the plunger's stroke.

According to basic principles of physics, the pressure exerted by an ideal spring within its normal operating range is directly proportional to its elastic force; this, in turn, is directly proportional to the spring's linear compression. In practice, therefore, the pressure exerted on the plunger's stopper decreases approximately linearly as the spring 30 expands, producing a progressively decreasing flow rate of medication out of the syringe.

The medication tubing 31 attached to the syringe is equipped with a luer-lock or similar fitting 32 for connection with the other components of the invention. Directly downstream is an injection port 34 mounted on a Y fitting, provided for use in the process of charging the syringe 20 with medication, as mentioned above, followed by a flow controller 36. The flow controller consists of a micro-bore cannula of a specific inside diameter and length to provide the necessary flow restriction and pressure drop for producing, in cooperation with the syringe 20, the desired flow rate of anesthetic to the patient. The flow controller 36 is obviously placed downstream of the injection port 34 to avoid interference with the process of charging the syringe. Through another luer-lock or similar fitting, the flow controller 36 is connected to a medication catheter 38 that is provided for placement into the surgical site S. Finally, a hypodermic needle 40 is provided for use during the procedure of placing the catheter 38 into the site S through a puncture P in the skin of the patient.

Figure 3:
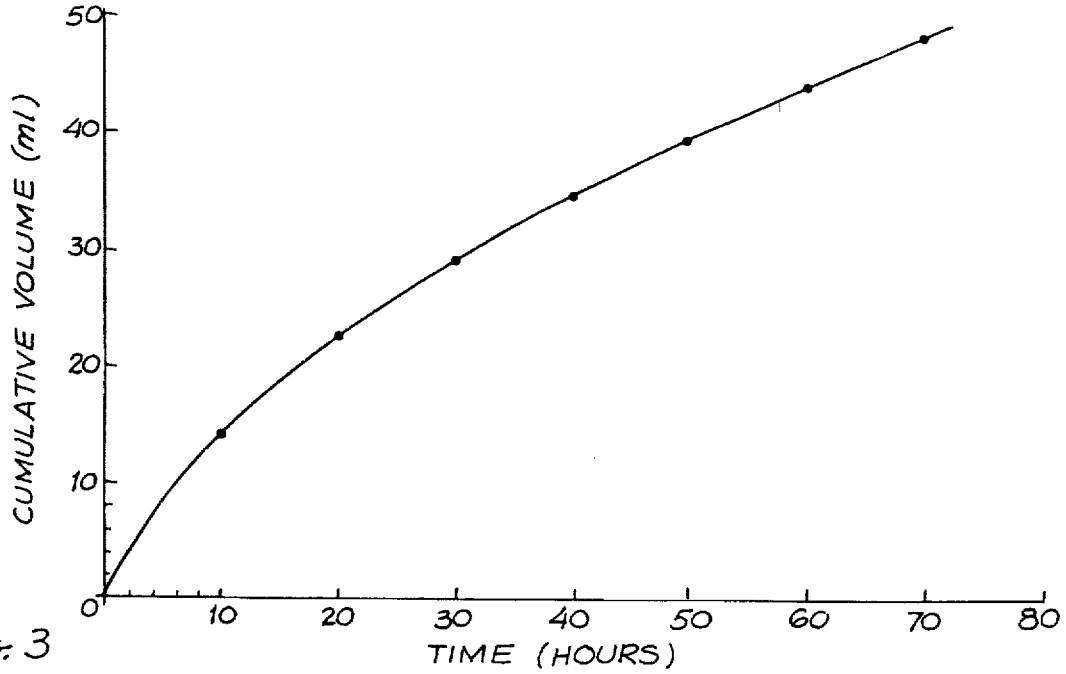
FIG. 3 is a representative plot of the cumulative volume of medication administered by the apparatus of the invention as a function of time.

In order to determine the precise specifications of the spring 30 and of the micro-bore cannula contained in the flow controller 36, experiments were conducted with medications currently used in anesthesia. For example, the drugs marketed by Winthrop Pharmaceuticals under the trademark "Marcaine" (0.25% HCl solution) and by Astra Pharmaceutical Products, Inc. under the name "Xylocane" (1% HCl solution) were tested over a three-day period of administration. The syringe 20 was charged with 50 ml of medication, well within the maximum recommended dosage for safety, and various sizes of springs and cannulae were used in the apparatus of the invention in order to determine experimentally what combination would provide the required delivery rates. It was found that a spring capable of producing an initial pressure of 12 psi, decreasing to 5 psi with 5 ml of liquid left in the syringe, in combination with a cannula ¼ inch long with an inside diameter of 0.0016 inches, produces the desired clinical rate for these drugs. Specifically, over a period of ten tests, the anesthetic was delivered through the system at a rate of 23.4 ml (±3.5 ml) during the first 24 hour period, 14.1 ml (±2.1 ml) during the second 24 hour period, and 10.0 ml (±1.5 ml) during the third 24 hour period. These rates are considered clinically optimal for post-operative anesthesia. FIG. 3 illustrates in graphical form the cumulative volume of medication administered to the patient in a typical run.

Referring to the mode of operation of this invention, the following steps are performed. The appropriate amount of medication is loaded into the spring-loaded syringe 20 with a regular injection syringe and needle through the port 34 according to standard safety procedure to avoid air entrainment. The point of the hypodermic needle 40 is pushed from inside the surgical wound S to penetrate away from the site to be medicated, and then pushed outside through the skin at a point P as far away from the site as possible. The end of the catheter 38 is inserted into the needle and threaded through it all the way to the surgical site, as illustrated in FIG. 1. Then, the needle is pulled out leaving the catheter in place in the surgical site, carefully avoiding introducing it into the epidural space. Finally, the syringe 20 is connected to the catheter through the flow controller 36 for the delivery of the medication. The catheter can safely remain in place for up to three days, which is considered a normal period of post-operative anesthetic treatment.

Figure 2:
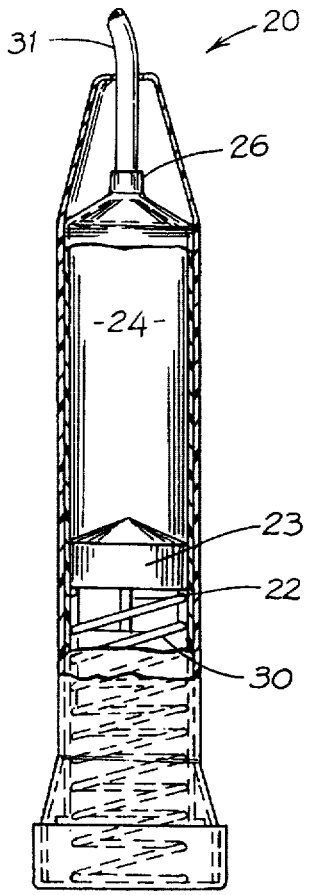
FIG. 2 is a cross-section of an elevational view of one embodiment of the spring-loaded syringe shown in FIG. 1.

With the exception of the spring-loaded syringe, all the components described above constitute standard medical equipment currently available in commerce. For example, a standard injection port and luer-lock fittings were used; the medication tubing was medical grade flexible PVC tubing; the catheter was 8 inch long and 22 gauge; and the placement needle was a standard 18 gauge hypodermic needle. The spring-loaded syringe was obtained by mounting a standard spring in a regular syringe so that it produced the necessary pressure against the plunger's stopper, as illustrated in FIG. 2.

While the embodiment shown in the figures features the specific shapes therein described, the invention can obviously take other shapes with equivalent functionality and utility. In fact, any shape for any of the components that retains the functional characteristics described above provides an acceptable apparatus to practice the invention. The capacity of the spring-loaded syringe and the size of all other components can be varied in obvious ways to produce different flow rates without affecting the scope of this disclosure. Similarly, a variety of other components could be introduced by one skilled in the art to fit the particular needs of specific applications. Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

What I claim as my invention is:

1. A method for the dispensation of post-surgical anesthesia at a continuous and progressively decreasing administration rate, comprising the following steps:

(a) providing a spring-loaded syringe, with sufficient capacity to hold a predetermined amount of anesthetic medication as required for the administration of post-surgical anesthesia, wherein the tip of said spring-loaded syringe is attached to a segment of flexible tubing ending with a luer-lock fitting;

(b) connecting an injection port to said spring-loaded syringe for charging it with medication contained in a regular syringe by injecting it into said injection port against the back pressure exerted by the stopper of said spring-loaded syringe, wherein the upstream branch of said injection port is attached to a segment of flexible tubing ending with a luer-lock fitting cooperatively engaged with the corresponding fitting attached to said spring-loaded syringe;

(c) connecting one side of a flow controller downstream of said injection port, said flow controller consisting of a micro-bore cannula of specific dimensions to produce a desired pressure drop, through which the medication is passed as a result of the pressure exerted by said stopper of the spring-loaded syringe, wherein the other side of said flow controller is connected to a segment of flexible tubing ending with a luer-lock fitting;

(d) connecting one end of a catheter to the luer-lock fitting on the downstream side of said flow controller;

(e) pushing a catheter placement needle, from the inside of a surgical wound and under the skin, as far away from the site to be medicated as possible, and then pushing it outside through the skin;

(f) threading the end of said catheter through the needle and pushing it through all the way to the surgical site;

(g) pulling said catheter placement needle out leaving the catheter in place in the surgical site; and (h) charging said spring-loaded syringe with medication through said injection port and allowing it to flow through the system into the surgical site for the required treatment period.

2. The method described in claim 1, wherein said spring-loaded syringe has the capacity of 50 ml.

3. The method described in claim 2, wherein said spring-loaded syringe exerts a pressure of approximately 12 psi when fully charged with said anesthetic medication and a pressure of approximately 5 psi with 5 ml remaining in the barrel.

4. The method described in claim 3, wherein said micro-bore cannula in said flow controller is approximately ¼ inch in length and 0.0016 inch in inside diameter.

5. The method described in claim 4, wherein said flexible tubing consists of medical grade PVC tubing.

6. The method described in claim 5, wherein said catheter consists of an 8 inch long 22 gauge catheter.

7. The method described in claim 6, wherein said catheter placement needle consists of an 18 gauge hypodermic needle.

*8. A method for the direct, low-flow-rate dispensation of post-surgical analgesia nonsystematically, at a progressively decreasing administration rate, into a cavity of a surgical site in a patient for the localized relief of pain in that site only, comprising the following steps:*

*(a) providing a spring-loaded syringe for dispensing analgesic medication, said syringe having sufficient capacity to hold a predetermined amount of analgesic medication as required for an administration of post-surgical analgesia and being adapted for administration at a progressively decreasing rate;*

*(b) providing a delivery means connected to said syringe for delivering the analgesic medication directly into the surgical site; and*

*(c) controlling the flow of analgesic medication into the cavity of the surgical site from said syringe and through said delivery means at a progressively decreasing rate not to exceed 25 ml per 24-hour period for a required treatment period.*

*9. The method described in claim 8, wherein said delivery means comprises control means for regulating the flow rate of analgesic medication being dispensed from said syringe.*

*10. The method described in claim 9, wherein said control means for regulating the flow rate of analgesic medication consists of a micro-bore cannula.*

*11. The method described in claim 8, wherein said syringe is capable of delivering the analgesic medication at a continuous administration rate during the required treatment period.*

*12. A method for the direct, low-flow-rate dispensation of post-surgical analgesia nonsystematically, at a progressively decreasing administration rate, into a cavity of a surgical site in a patient for the localized relief of pain in that site only, comprising the following steps:*

*(a) providing a first means for dispensing analgesic medication, said first means having sufficient capacity to hold a predetermined amount of analgesic medication as required for an administration of post-surgical analgesia and being adapted for administration at a progressively decreasing rate;*

*(b) providing a second means connected to said first means for delivering the analgesic medication directly into the surgical site; and*

*(c) controlling the flow of analgesic medication into the cavity of the surgical site from said first means and through said second means at a progressively decreasing rate not to exceed 25 ml per 24-hour period for a required treatment period;*

*wherein said step (b) is accomplished by providing a catheter connected to said first means and a catheter placement needle; by pushing the catheter placement needle inside a wound at a surgical site so as to cause the needle to emerge from the skin of the patient; by threading the end of said catheter through the needle and placing it within the cavity of the surgical site; and by pulling said catheter placement needle out leaving the catheter in place in the surgical site.*

*13. The method described in claim 12, wherein said second means comprises means for regulating the flow rate of analgesic medication being dispensed from said first means.*

*14. The method described in claim 13, wherein said means for regulating the flow rate of analgesic medication consists of a micro-bore cannula.*

*15. A method for the direct, low-flow-rate dispensation of post-surgical analgesia nonsystematically, at a progressively decreasing administration rate, into a cavity of a surgical site in a patient for the localized relief of pain in that site only, comprising the following steps:*

*(a) providing a spring-loaded syringe for dispensing analgesic medication, said syringe having sufficient capacity to hold a predetermined amount of analgesic medication as required for an administration of post-surgical analgesia and being adapted for administration at a progressively decreasing rate;*

*(b) providing a delivery means connected to said syringe for delivering the analgesic medication directly into the surgical site; and*

*(c) controlling the flow of analgesic medication into the cavity of the surgical site from said syringe and through said delivery means at a progressively decreasing rate.*

*16. A method for the direct, low-flow-rate dispensation of post- surgical analgesia nonsystematically, at a progressively decreasing administration rate, into a cavity of a surgical site in a patient for the localized relief of pain in that site only, comprising the following steps:*

*(a) providing a first means for dispensing analgesic medication, said first means having sufficient capacity*

*to hold a predetermined amount of analgesic medication as required for an administration of post-surgical analgesia and being adapted for administration at a progressively decreasing rate;*

(*b*) *providing a second means connected to said first means for delivering the analgesic medication directly into the surgical site; and*

(*c*) *controlling the flow of analgesic medication into the cavity of the surgical site from said first means and through said second means at a progressively decreasing rate for a required treatment period;*

*wherein said step (b) is accomplished by providing a catheter connected to said first means and a catheter placement needle; by pushing the catheter placement needle inside a wound at a surgical site so as to cause the needle to emerge from the skin of the patient; by threading the end of said catheter through the needle and placing it within the cavity of the surgical site; and by pulling said catheter placement needle out leaving the catheter in place in the surgical site.*

* * * * *